United States Patent
Obradovic et al.

(10) Patent No.: US 8,496,697 B2
(45) Date of Patent: Jul. 30, 2013

(54) STENT GRAFT

(75) Inventors: Milisav Obradovic, Lörrach (DE); Rainer Bregulla, Balingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 80 days.

(21) Appl. No.: 13/057,261

(22) PCT Filed: May 18, 2009

(86) PCT No.: PCT/EP2009/003529
§ 371 (c)(1),
(2), (4) Date: May 9, 2011

(87) PCT Pub. No.: WO2010/015291
PCT Pub. Date: Feb. 11, 2010

(65) Prior Publication Data
US 2011/0213455 A1 Sep. 1, 2011

(30) Foreign Application Priority Data
Aug. 4, 2008 (EP) ..................... 08013947

(51) Int. Cl.
*A61F 2/06* (2006.01)
(52) U.S. Cl.
USPC ........................ 623/1.11; 623/1.16
(58) Field of Classification Search
USPC ....... 623/1.11, 1.12, 1.13, 1.15, 1.2; 606/194, 606/198
See application file for complete search history.

(56) References Cited

U.S. PATENT DOCUMENTS

| 5,667,523 | A | * | 9/1997 | Bynon et al. | 623/1.13 |
| 5,916,264 | A | * | 6/1999 | Von Oepen et al. | 623/1.15 |
| 7,294,145 | B2 | * | 11/2007 | Ward | 623/1.11 |
| 2002/0010507 | A1 | * | 1/2002 | Ehr et al. | 623/1.16 |
| 2005/0192662 | A1 | * | 9/2005 | Ward | 623/1.16 |
| 2006/0195175 | A1 | * | 8/2006 | Bregulla | 623/1.15 |

FOREIGN PATENT DOCUMENTS

| EP | 0878173 | 11/1998 |
| WO | WO 2004021929 | 3/2004 |
| WO | WO 2010015291 | 2/2010 |

* cited by examiner

*Primary Examiner* — Tuan V Nguyen
(74) *Attorney, Agent, or Firm* — Workman Nydegger; Jonathan D. Feuchtwang

(57) ABSTRACT

A stent-graft including an inner stent having a wall structure including juxtaposed strut-patterns with interconnected struts and connectors connecting the strut-patterns is described. The wall structure of the inner stent has a predetermined length. An outer stent is coaxially arranged around the inner stent and has a wall structure including juxtaposed strut-patterns with interconnected struts and connectors connecting the strut-patterns. The wall structure of the outer stent has a predetermined length and a flexible stretchable material layer arranged between the inner stent and the outer stent. The wall structure of the inner stent has a design differing from the design of the wall structure of the outer stent and the length of the inner stent is equal to the length of the outer stent.

8 Claims, 5 Drawing Sheets

STENT GRAFT

CROSS-REFERENCE TO RELATED APPLICATIONS

This application is a U.S. Nationalization of PCT Application Number PCT/EP2009/003529 filed May 18, 2009 which claims the benefit of European Patent Application No. 08013947.0 filed Aug. 4, 2008, the entireties of which are incorporated herein by reference.

BACKGROUND

1. Field of the Invention

The present invention relates to a stent graft.

2. Relevant Technology

Stent grafts generally comprise an inner stent and an outer stent using similar wall structures including the same strut-patterns and a flexible membrane or stretchable material layer interposed between the inner and outer stent. When the balloon of the catheter is inflated the inner stent is less expanded than the outer stent and therefore physically exhibits a bigger recoil force compared to the more expanded outer stent. Hence the smaller radially acting contact force of the expanded inner stent onto the outer stent deteriorates the desired connecting performance of the stent-graft. Furthermore stent-grafts having thinner walls to be more flexible are often damaged or destroyed during welding to fix both stents to one another

BRIEF SUMMARY

It is, therefore, an object underlying the present invention to provide a stent-graft that is able to solve the above mentioned problems occurring to prior art stent-grafts.

The solution of this object is achieved by the features of claim 1.

The stent-graft according to one embodiment of the present invention includes an inner stent having a wall structure including juxtaposed strut-patterns with interconnected struts and connectors connecting the strut-patterns, the wall structure of the inner stent having a predetermined length, an outer stent coaxially arranged around the inner stent and having a wall structure including juxtaposed strut-patterns with interconnected struts and connectors connecting the strut-patterns, the wall structure of the outer stent having a predetermined length and a flexible stretchable material layer arranged between the inner stent and the outer stent, wherein the wall structure of the inner stent has a design differing from the design of the wall structure of the outer stent and wherein the length of the inner stent is equal to the length of the outer stent.

According to an embodiment of the stent-graft of the present invention, the struts of the inner stent are formed shorter than the struts of the outer stent and the connectors of the inner stent are longer than the connectors of the outer stent.

According to a further embodiment of the stent-graft of the present invention, the struts of the inner stent are formed shorter than the struts of the outer stent and the connectors of the inner stent have the same length as the connectors of the outer stent and the inner stent has at least one additional strut pattern.

According to a still further embodiment of the stent-graft of the present invention, the struts of the inner stent are formed shorter than the struts of the outer stent and the straight connectors of the inner stent are shorter than the straight connectors of the outer stent, the s-shaped connectors of the inner and outer stent having the same length and width, and the inner stent has at least one additional strut pattern.

According to a yet further embodiment of the stent-graft of the present invention, the crown ends of the outer and inner stents include a welding zone having a welding point to fix the outer and inner stents to one another.

BRIEF DESCRIPTION OF THE DRAWINGS

Further features and advantages of the present invention will become apparent from the following description of preferred embodiments with reference to the appended drawings, wherein.

DETAILED DESCRIPTION

Figure 1:
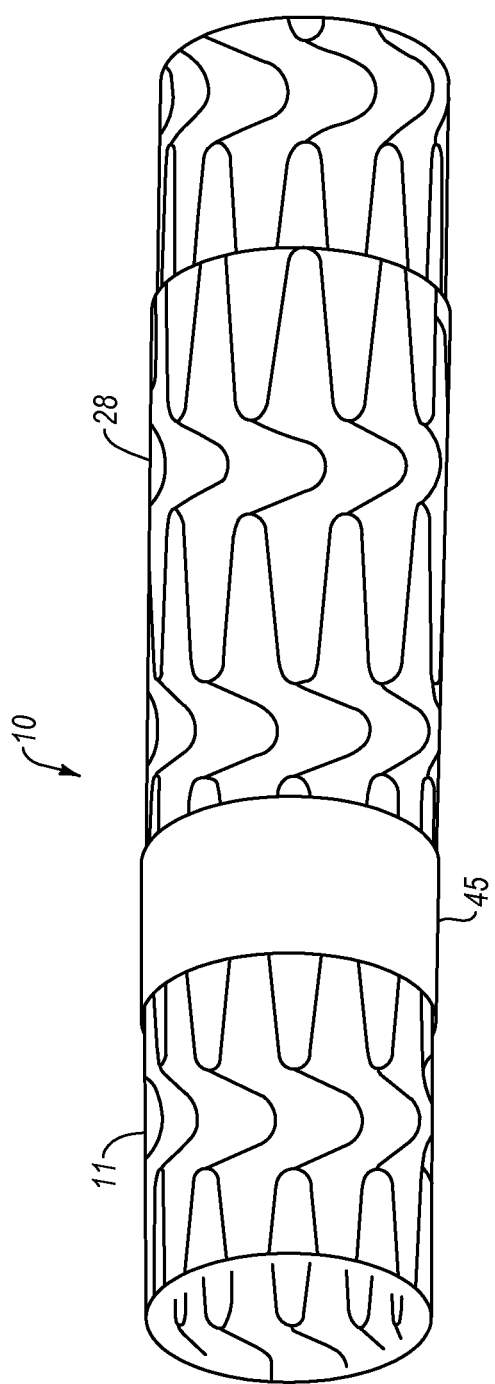
FIG. 1 shows an enlarged perspective view of a common stent-graph.

FIG. 1 shows an enlarged perspective view of a stent-graph 10. An inner stent 11 is connected to an outer stent 28 and of a flexible stretchable material layer 45 is disposed therebetween. The inner stent 11 and the outer stent 28 each comprise a design of the wall structure which is different from each other.

Figure 2A:
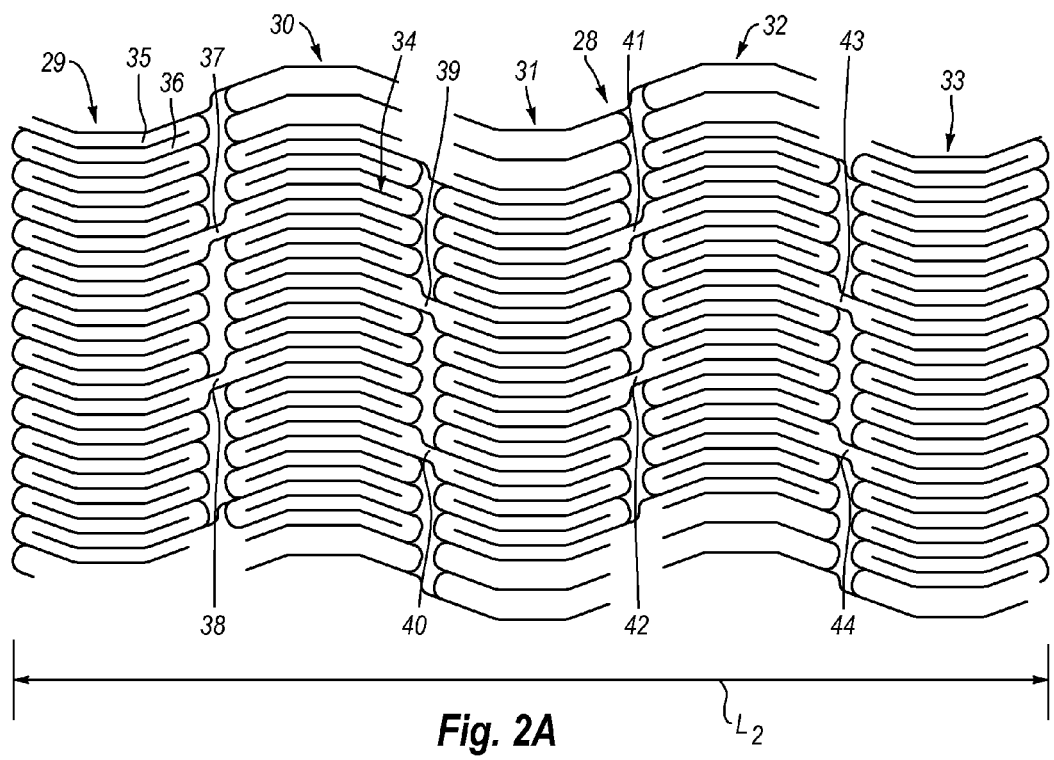
FIG. 2A shows an enlarged plan view of a wall structure of an outer stent of the stent-graft according to the present invention.

FIG. 2A shows an enlarged plan view of the wall structure 34 of the outer stent 28 of the stent-graft 10 according to the present invention having a predetermined length $L_2$. As can be seen from FIG. 2A, the design of the wall structure 34 of the outer stent 28 includes five juxtaposed strut patterns 29-33 with interconnected struts 35, 36 and connectors 37-44 connecting the strut patterns 29-33.

Figure 2B:
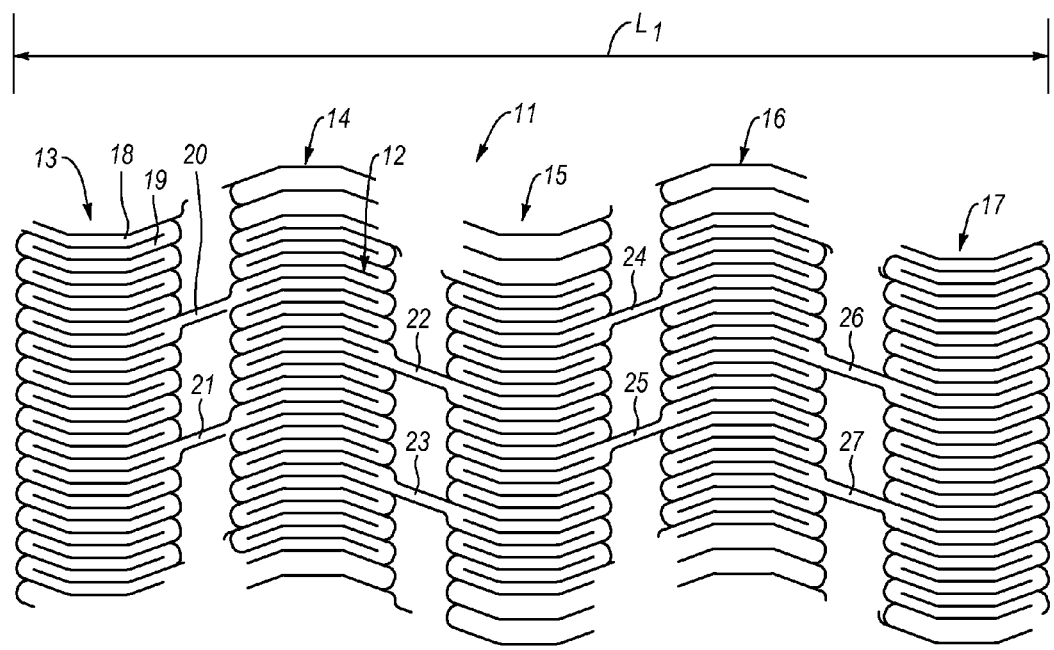
FIG. 2B shows an enlarged plan view of a wall structure of an inner stent of the stent-graft according to the present invention.

FIG. 2B shows an enlarged plan view of the wall structure 12 of the inner stent 11 of the stent-graft 10 according to the present invention having a predetermined length $L_1$ which is equally long as the predetermined length $L_2$ of the outer stent 28. As shown in FIG. 2B, the design of the wall structure 12 of the inner stent 11 includes five juxtaposed strut patterns 13-17 with interconnected struts 18, 19 and connectors 20-27 connecting the strut patterns 13-17. According to the present invention, the design of the wall structure 12 differs from the design of the wall structure 34 in that shorter strut patterns 13-17 and longer connectors 20-27 are provided connecting the strut patterns 13-17 to define the same overall length $L_1$ as the length $L_2$ of the outer stent 28 illustrated in FIG. 2A.

In a further embodiment of the stent-graft 10 of the present invention, the struts 18, 19 of the inner stent 11 are shorter than the struts 35, 36 of the outer stent 34. Moreover, the connectors 20-27 of the inner stent 11 have the same length as the connectors of the outer stent 28 and the inner stent 11 has at least one additional strut pattern to define the same overall length $L_1$ as the length $L2$ of the outer stent 28.

Due to the inner stent 11 having a different stent design either with shorter struts and slightly longer connectors 20-27 or at least one additional strut pattern along the predetermined length $L_1$ being equal to $L_2$ of the outer stent the radial connecting force of the inner stent 11 is increased during expansion and both stents 11, 28 are pressed stronger to one another. Furthermore, the resultant difference in foreshortening as a result of the differing expansion of the inner and outer stents 11, 28 of the stent-graft 10 of the present invention is favorably compensated.

Figure 3A:
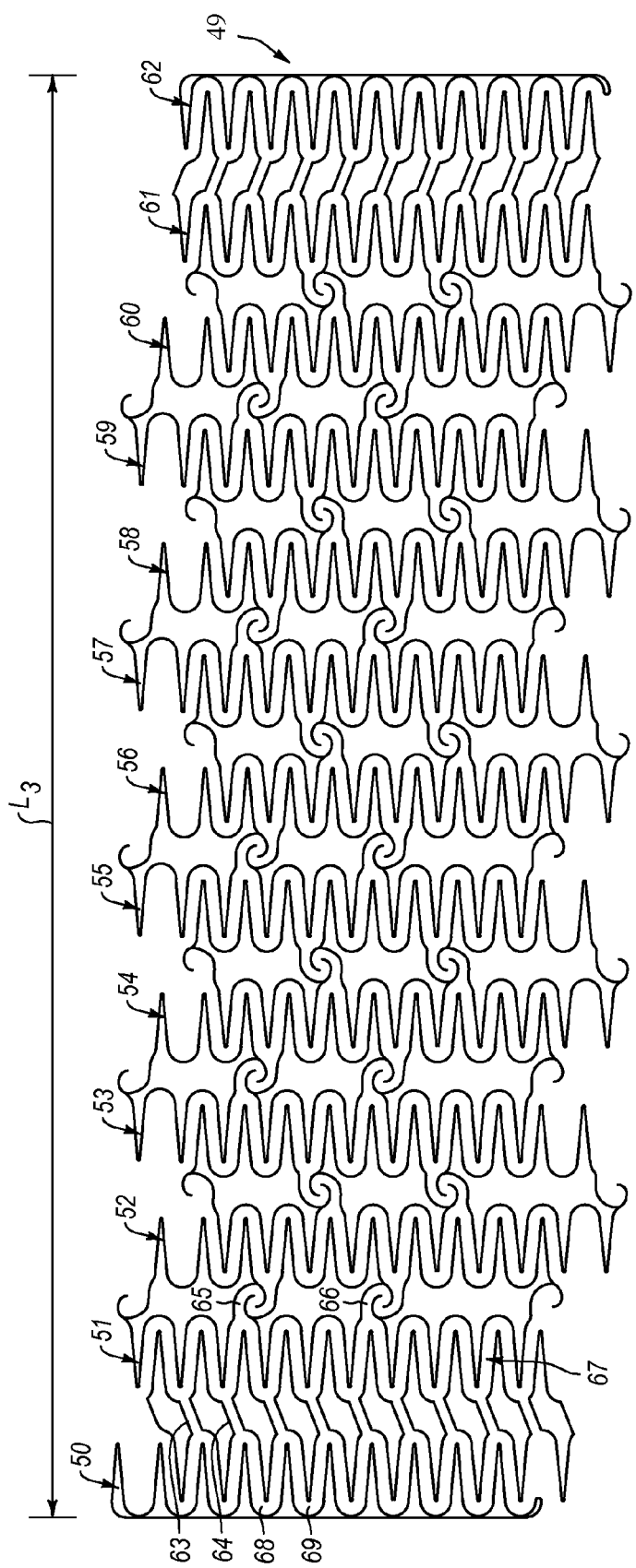
FIG. 3A shows an enlarged view of a further embodiment of a wall structure of the outer stent of the stent-graft according to the present invention.
Figure 3B:
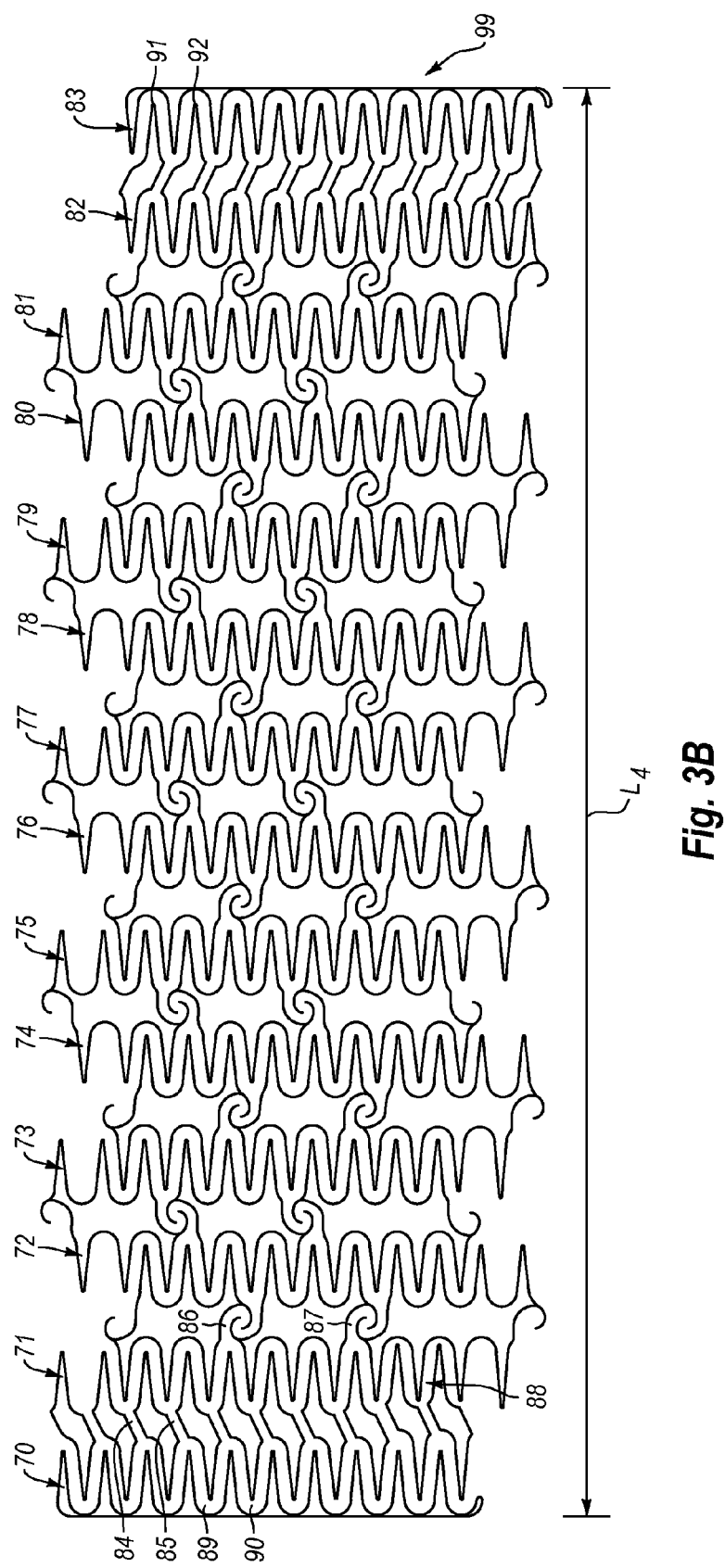
FIG. 3B shows an enlarged view of a further embodiment of a wall structure of the inner stent of the stent-graft according to the present invention.

FIG. 3A shows an enlarged plan view of the wall structure 67 of the outer stent 49 of the stent-graft 10 according to the present invention having a predetermined length $L_3$ which is equally long as the predetermined length $L_4$ of the inner stent 99 depicted in FIG. 3B. As can be seen from FIG. 3A, the design of the wall structure 67 of the outer stent 49 includes thirteen juxtaposed strut patterns 50-62 with interconnected struts 68, 69 and straight connectors 63, 64 connecting the strut patterns 50, 51 as well as the strut patterns (61, 62). The strut patterns 52 to 60 are interconnected with s-shaped connectors 65, 66.

FIG. 3B shows an enlarged plan view of the wall structure 88 of the inner stent 99 of the stent-graft 10 according to the present invention having a predetermined length $L_4$ which is equally long as the predetermined length $L_3$ of the outer stent 49 of FIG. 3A. As can be seen from FIG. 3B, the design of the wall structure 88 of the inner stent 99 includes fourteen juxtaposed strut patterns (70-83) with interconnected struts (89, 90) and straight connectors (84-85) connecting the strut patterns (70-71) as well as the strut patterns (82-83). The strut patterns (72-81) are interconnected with s-shaped connectors 86, 87 having the same length and width as the s-shaped connectors (65, 66).

This alternative embodiment (having a stent design with an increased number of shorter struts and slightly shorter straight connectors 84, 85, 91, 92 between the adjacent first two and last two strut patterns 70, 71; 82, 83 and at least one additional strut pattern along the predetermined length $L_4$ being equal to $L_3$ of the outer stent results in an increased radial connecting force of the inner stent 99 during expansion and both stents 49, 99 are pressed stronger to one another. By adapting the length of the straight connectors 84, 85, 91, 92, while the s-shaped connectors each keep the same length and width, an adjustment of the identical overall length $L_3$, $L_4$ of the outer and inner stents can be achieved. It should be understood that a variety of stent designs can be used to enhance the radial connecting force of the inner stent in relation to the outer stent by shortening the individual connectors to hence eliminate the above mentioned drawback of the prior art stent-graft.

Figure 4:
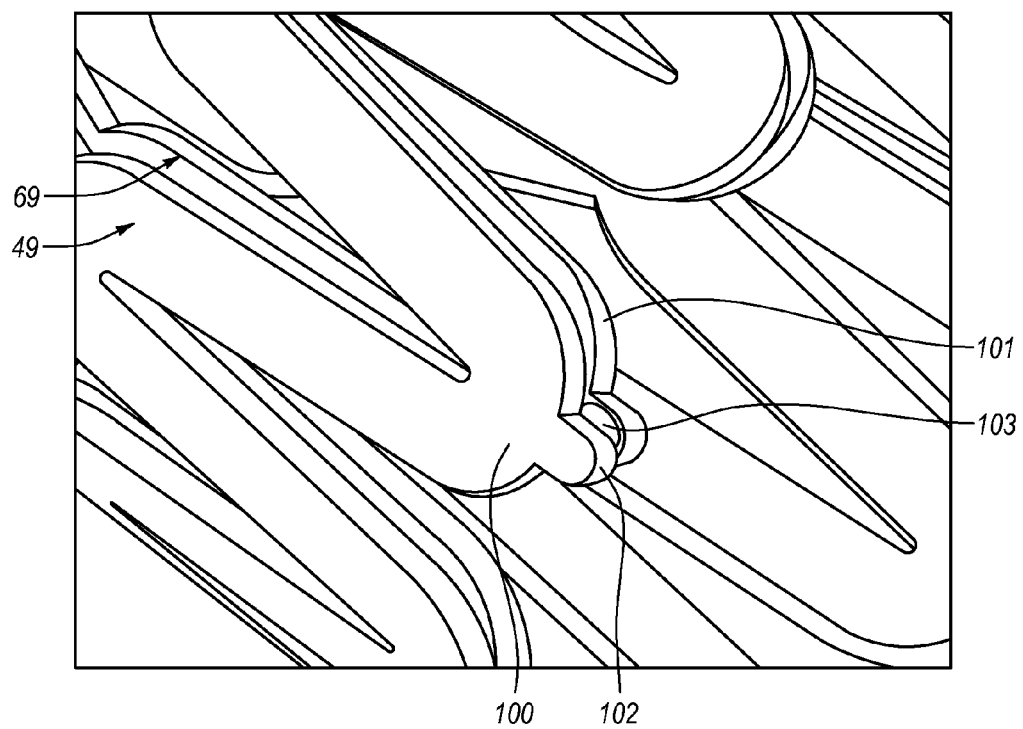
FIG. 4 shows an enlarged view of a further embodiment of a welding zone at the crown ends of the outer and inner stents of the stent-graft according to the present invention.

FIG. 4 shows an enlarged view of a further embodiment of the stent-graft 10 having a welding zone 102 at a crown end 100 of the outer stent 49 and a crown end 101 of the inner stent 99 comprising a welding point 103 which fixes both stents 49, 99 to one another. Thus, the use of thinner walls thicknesses for the stents for decreasing the stiffness, reducing the overall profile and increasing the flexibility of the stents can be achieved without causing problems during the welding process during production.

In addition to the written disclosure reference is herewith made explicitly to the disclosure of the invention in FIGS. 1 to 3B.

The invention claimed is:

1. A stent-graft comprising:
   an inner stent having a wall structure including juxtaposed strut-patterns with interconnected struts and connectors connecting the strut-patterns, the wall structure of the inner stent having a predetermined length;
   an outer stent coaxially arranged around the inner stent and having a wall structure including juxtaposed strut-patterns with interconnected struts and connectors connecting the strut-patterns, the wall structure of the outer stent having a predetermined length; and
   a flexible stretchable material layer arranged between the inner stent and the outer stent, the wall structure of the inner stent having a design differing from the design of the wall structure of the outer stent, and the length of the inner stent being equal to the length of the outer stent;
   wherein the struts of the inner stent are shorter than the struts of the outer stent and wherein straight connectors of the inner stent are provided between strut patterns at both ends of the inner stent, the connectors being shorter than straight connectors of the outer stent between strut patterns at both ends of the outer stent; and
   wherein s-shaped connectors connect all the remaining strut patterns of the inner and outer stents except the two strut patterns at the ends of the inner and outer stent.

2. The stent-graft according to claim 1, wherein a welding zone comprising a welding point is arranged at crown ends of the outer and inner stents for fixing the inner and outer stents to one another.

3. The stent graft according to claim 1, wherein the inner stent has at least one additional strut pattern.

4. The stent graft according to claim 1, wherein the s-shaped connectors of the inner stent have same length and width as the s-shaped connectors of the outer stent.

5. A stent-graft comprising:
   an inner stent having a wall structure including juxtaposed strut-patterns with interconnected struts and connectors connecting the strut-patterns, the wall structure of the inner stent having a predetermined length;
   an outer stent coaxially arranged around the inner stent and having a wall structure including juxtaposed strut-patterns with interconnected struts and connectors connecting the strut-patterns, the wall structure of the outer stent having a predetermined length; and
   a flexible stretchable material layer arranged between the inner stent and the outer stent, the wall structure of the inner stent having a design differing from the design of the wall structure of the outer stent, and the length of the inner stent being equal to the length of the outer stent, the struts of the inner stent being shorter than the struts of the outer stent,
   wherein straight connectors of the inner stent are provided between strut patterns at both ends of the inner stent and the connectors of the inner stent are shorter than straight connectors of the outer stent between strut patterns at both ends of the outer stent;
   wherein s-shaped connectors connect all the remaining strut patterns of the inner and outer stents except the two strut patterns at the ends of the inner and outer stent.

6. The stent-graft according to claim 5, wherein the inner stent has at least one additional strut pattern.

7. The stent graft according to claim 5, wherein the s-shaped connectors of the inner stent have same length and width as the s-shaped connectors of the outer stent.

8. The stent-graft according to claim 5, wherein a welding zone comprising a welding point is arranged at crown ends of the outer and inner stents for fixing the inner and outer stents to one another.

* * * * *

UNITED STATES PATENT AND TRADEMARK OFFICE
CERTIFICATE OF CORRECTION

PATENT NO.        : 8,496,697 B2  
APPLICATION NO.   : 13/057261  
DATED             : July 30, 2013  
INVENTOR(S)       : Obradovic et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 176 days.

Signed and Sealed this
Fifteenth Day of September, 2015

Michelle K. Lee
*Director of the United States Patent and Trademark Office*